United States Patent [19]

Eigen et al.

[11] Patent Number: 5,643,559

[45] Date of Patent: Jul. 1, 1997

[54] DEODORANT COMPOSITIONS COMPRISING INHIBITORS OF ODOR-PRODUCING AXILLARY BACTERIAL EXOENZYMES

[75] Inventors: Edward Eigen, East Brunswick; Claudia Froebe, Piscataway, both of N.J.

[73] Assignee: Colgate-Palmolive Company, New York, N.Y.

[21] Appl. No.: 206,919

[22] Filed: Mar. 4, 1994

Related U.S. Application Data

[63] Continuation of Ser. No. 785,585, Oct. 30, 1991, abandoned.
[51] Int. Cl.$^6$ .................................................. A61K 7/36
[52] U.S. Cl. ................................... 424/67; 424/65
[58] Field of Search ........................... 424/65, 67

[56] References Cited

U.S. PATENT DOCUMENTS

| | | | |
|---|---|---|---|
| 1,823,721 | 9/1931 | Bennett | 424/67 |
| 1,984,669 | 12/1934 | Taub | 424/67 |
| 2,087,162 | 7/1937 | Moore | 424/67 |
| 2,210,014 | 8/1940 | Teller | 424/67 |
| 2,236,387 | 3/1941 | Wallace et al. | 167/90 |
| 2,857,315 | 10/1958 | Teller | 167/90 |
| 3,172,817 | 3/1965 | Leapoid et al. | 167/90 |
| 3,255,082 | 6/1966 | Barton | 107/90 |
| 3,553,316 | 1/1971 | Rubino | 424/68 |
| 3,917,815 | 11/1975 | Kalopissis et al. | 424/45 |
| 3,996,346 | 12/1976 | Staffier et al. | 424/67 |
| 4,172,123 | 10/1979 | Lowicki | 424/67 |
| 4,339,432 | 7/1982 | Ritchey et al. | 424/54 |
| 4,382,079 | 5/1983 | Marschner | 424/65 |
| 4,425,325 | 1/1984 | Ritchey et al. | 424/54 |
| 4,440,741 | 4/1984 | Marschner | 424/65 |
| 4,440,742 | 4/1984 | Marschner | 424/65 |
| 4,565,693 | 1/1986 | Marschner | 424/67 |

FOREIGN PATENT DOCUMENTS

| | | |
|---|---|---|
| 0024176 | 8/1980 | European Pat. Off. . |
| 2818321 | 11/1978 | Germany . |
| 52-61239 | 5/1977 | Japan . |
| 701546 | 12/1953 | United Kingdom . |
| 1439403 | 6/1976 | United Kingdom . |
| 2052978 | 2/1981 | United Kingdom . |
| 2109685 | 6/1983 | United Kingdom . |

OTHER PUBLICATIONS

Charig A, Froebe C, Eigen E. (1991) J. Soc. Cosmet. Chem 42(3) 133–146. (Abstract).

"Auxillary malodor production: A new mechanism", *J. Soc. Cosmet. Chem.*, vol. 41, pp. 173–185 (May/Jun. 1990).

"Inhibitor of odor–producing auxillary bacterial exoenzymes" *J. Soc. Cosmet. Chem.*, vol. 42, pp. 133–145 (May/Jun. 1991).

"Chemical and Bacteriological Aspects of Antiperspirants and Deodorants", *J. Soc. Cosmet. Chem.*, vol. 7:2, pp. 85–105 (1956).

Dubsky et.al., *Chemical Abstracts*, vol. 24, p. 4722, (1930).
"Letters to the Editor", by E. Eigen, *J. Soc. Cosmet. Chem.* vol. 41, pp. 147–149 (Mar./Apr. 1990).

*Primary Examiner*—C. Warren Ivy
*Assistant Examiner*—Evelyn Huang
*Attorney, Agent, or Firm*—Richard J. Ancel; James M. Serafino

[57] ABSTRACT

Deodorant compositions and a method of inhibiting bacterial exoenzymes responsible for the production of steroidal axillary malodor. The deodorant composition contains a cosmetic vehicle comprising inorganic acids, organic acids or water soluble metal salts of fatty acids is combined with a deodorant active material, selected from the group consisting of Zn++ compounds, which is an inhibitor of bacterial exoenzymes responsible for the production of steroidal axillary malodor. The deodorant active materials of the invention directly inhibit the bacterial exoenzymes responsible for the production of steroidal axillary malodor rather than neutralizing unpleasant odors through chemical interaction and indirect inhibition of bacterial growth. These materials may be dissolved or suspended in a cosmetic vehicle in the form of a soap, lotion, fluid, cream, gel stick, powder or spray to provide a deodorant composition to prevent axillary odor without disturbing the natural flora of the axilla.

9 Claims, 5 Drawing Sheets

DEODORANT COMPOSITIONS COMPRISING INHIBITORS OF ODOR-PRODUCING AXILLARY BACTERIAL EXOENZYMES

This is a continuation of application Ser. No. 07/785,585 filed on Oct. 30, 1991, abandoned.

FIELD OF INVENTION

This invention generally relates to deodorant compositions comprising deodorant active materials which are inhibitors of odor-producing axillary bacterial exoenzymes. More particularly, it concerns compounds which inhibit the bacterial exoenzymes aryl sulfatase and beta glucuronidase responsible for the production of steroidal axillary malodor.

BACKGROUND ART

The human axilla is populated with two classes of sweat glands: eccrine and apocrine. The eccrine glands produce a watery secretion in response to heat, and the apocrine glands produce microdroplets of a viscous secretion in response to emotional stress. Aprocrine sweat is a complex mixture containing cholesterol, steroids, and other lipids, as well as 10% protein. It is well established that axillary odor is generated from apocrine secretion. Although the sterile fluid is odorless, bacterial action on certain components present in sweat produces the characteristic underarm odor.

It was initially viewed that any or all of the axillary population could cause odor, but it was determined that odor was caused primarily by gram-positive type bacteria. The chemical source of axillary odor has been divided into two classes of odorants: short-chain fatty acids, e.g. isovaleric acid, and the androgen steroids, particularly 5-α-androstenol and 5-α-androstenone.

Class 1: short chain fatty acids isovaleric acid    $\underset{CH_1}{\overset{CH_3}{\diagdown}}CH-CH_2-COOH$ Class 2: androgen steroids 5, α-androst-16-en-3, β-ol Class 1: short chain fatty acids 5, α-androst-16-en-3-one A correlation exits between the composition of the underarm flora and the nature of the odor produced. Where the axillary microbial population is dominated by coryneform bacteria (lipophilic diphtheroids) the acrid odor of delta-16 steroids is apparent, whereas, if the axillary population is dominated by micrococci such as Staphylococcus epidermidis, the odor of isovaleric acid prevails. Pronounced axillary odor is further associated with the presence of the coryneform flora. The prior art has thus identified axillary steroids and have linked their presence with indigenous bacteria, however the mechanism of bacterial action in producing odor has remained uncertain.

In general, steroids are not water-soluble and are normally transported in body fluids as their water-soluble conjugates with sulfate or glucuronic acid. The present invention reveals that the origin of volatile free steroids in the axilla, thought to be responsible for axillary odor, are from the apocrine secretions which contain the steroids as their water-soluble conjugates. Conversion in vivo to the free steroid requires the action of hydrolytic enzymes. It is the production of these enzymes that represents the contribution of bacteria to the generation of underarm odor through the hydrolysis of steroid conjugates, as shown below. The sterile apocrine sweat deposits the water-soluble, odorless steroid conjugates onto hair and skin in the axilla, where enzymes secreted by local bacteria release the volatile, odorous, free steroids. The enzymes which hydrolyze the steroid esters can be any of several bacterial exoesterases—for example, beta-glucuronidase (beta-G) and aryl sulfatase (AS).

Mechanism for hydrolysis of steroid conjugates
in the production of axillary odorants 5-α-androst-16-en-3,β-ol glucuronide 5, α-androst-16-en-3, β-ol sulfate -continued
Mechanism for hydrolysis of steroid conjugates
in the production of axillary odorants The prior art has disclosed various compositions and methods of combating body odors in the formulation of deodorant compositions containing deodorant active agents. As an example, U.S. Pat. No. 4,565,693 to Marschner, assigned to the Applicant, discloses a deodorant composition containing zinc glycinate as a non-irritating effective deodorant agent which chemically neutralizes odoriferous compounds and inhibits bacterial growth.

The deodorant compositions in Marschner contain zinc glycinate in anhydrous or hydrated bis (glycino) forms. In Marschner it was originally thought that the deodorant active material possessed the dual function of reducing odor by indirectly inhibiting bacterial growth and chemically neutralizing body odors. Certain ingredients, such as inorganic acids, organic acids or water soluble metal salts of fatty acids were thought to deactivate the deodorant properties of the zinc glycinate deodorant formulations.

The present invention however has further provided a method of directly inhibiting bacterial exoenzymes responsible for the production of steroidal malodor. Deodorant active materials of the invention inhibit the bacterial exoenzymes secreted by local bacteria to prevent release of volatile, odorous, free steroids which are responsible for the axillary malodor. The deodorant active materials including Zn++ compounds, preferably zinc glycinate, function as bacterial exoenzyme inhibitors and are substantive to skin and hair.

Thus present practice to date has not yet provided deodorant compositions or methods of preventing steroidal axillary malodor through direct inhibition of bacterial exoenzymes. There is a need in the art for a method of inhibiting bacterial exoenzymes responsible for the production of steroidal axillary malodor. This invention is directed to the provision of such processes which have wide range applications in creating deodorant compositions. It would be appreciated that advantage over prior art methods of deodorizing would be obtained by providing an effective deodorant composition to prevent the production of steroidal axillary malodor without disturbing the natural flora of the axilla.

Accordingly, it is a broad object of the invention to provide deodorant compositions comprising deodorant active material, which are inhibitors of bacterial exoenzymes responsible for the production of steroidal axillary malodor, dissolved or suspended in a cosmetic vehicle.

A more specific object of the invention is to provide deodorant compositions comprising deodorant active material which inhibit the bacterial exoenzymes aryl sulfatase and beta glucuronidase responsible for the production of steroidal axillary malodor.

Another object of the invention is to provide a method of inhibiting bacterial exoenzymes responsible for the production of steroidal axillary malodor by dissolving or suspending a deodorant active material in a cosmetic vehicle to produce a deodorant composition to prevent the production of axillary odor.

A specific object of the invention is to provide deodorant compositions containing a deodorant active material that inhibits the odor-producing axillary bacterial exoenzymes, which may be in the form of a soap, lotion, fluid, cream, gel stick, powder or spray.

DISCLOSURE OF INVENTION

In the present invention, these purposes, as well as others which will be apparent, are achieved generally by providing a method of inhibiting bacterial exoenzymes responsible for the production of steroidal axillary malodor. The method comprises the steps of providing a cosmetic vehicle and dissolving or suspending a deodorant active material which is an inhibitor of bacterial exoenzymes responsible for the production of steroidal axillary malodor therein to produce a deodorant composition.

Aryl sulfatase and beta-glucuronidase are the primary bacterial exoenzymes responsible for producing steroidal axillary odor. The deodorant active materials are inhibitors of these exoenzymes and include Cu++, hexametaphosphate (SPORIX), D-glucaro-▲-lactone, EDTA, NTA, O-phenanthroline, Sodium sulfate or orthophosphate. The deodorant active material constitutes between 1–100% by weight of the composition.

The deodorant active material is dissolved or suspended in a cosmetic vehicle to provide a deodorant composition to prevent axillary malodor. The cosmetic vehicle can be in the form of a soap, lotion, fluid, cream, gel stick, powder or spray. The vehicle in the form of a soap or detergent comprising inorganic acids, organic acids or water soluble metal salts of fatty acids. The vehicle in the form of a lotion contains non-volatile polar or non-polar ingredients selected from the group consisting of polyhydric alcohols and emollient oils. Preferably the lotion comprises a liquid carrier of a lower alcohol or an aqueous alcoholic media. The vehicle in the form of a fluid is comprised of a suspending or thickening agent for use as a roll-on. The stick vehicle is comprised of a monohydric or polyhydric alcohol gelled with a fatty alcohol or fatty amide or combination thereof. The cream vehicle is comprised of an aqueous emulsion of a fatty material. The deodorant agent can further be suspended in a liquid vehicle comprised of a carrier liquid and a liquified gaseous propellant, in the form of a deodorant spray.

In an alternative embodiment of the invention, a cosmetic vehicle comprising inorganic acids, organic acids or water soluble metal salts of fatty acids is combined with a deodorant active material, selected from the group consisting of $Zn++$ compounds, which is an inhibitor of bacterial exoenzymes responsible for the production of steroidal axillary malodor. The deodorant active material is dissolved or suspended in the cosmetic vehicle to produce a deodorant composition which prevents steroidal axillary malodor. Any $Zn++$ compound may be employed in the invention if it is stable at the pH of the final composition and if it provides adequate levels of free $Zn++$ ions. A preferred deodorant active material is zinc-glycinate. Preferably, the deodorant active material constitutes over 50% by weight of the deodorant composition. The cosmetic vehicle of this embodiment can also be in the form of a soap, lotion, fluid, cream, gel stick, powder or spray.

Preferred applications of the materials of the invention include use in deodorant compositions. As used in these applications, the materials of invention may be provided in a number of vehicles such as water, soap, lotion, fluid, cream, gel stick, powder or spray to prevent axillary odor. Advantageously, the use of the deodorant compositions of the invention directly inhibit the bacterial exoenzymes responsible for the production of steroidal axillary malodor rather than neutralizing unpleasant odors through chemical interaction and indirect inhibition of bacterial growth. Further advantage is obtained by the invention by not disturbing the natural flora of the axilla.

Other objects, features and advantages of the present invention will be apparent when the detailed description of the preferred embodiments of the invention are considered in conjunction with the drawings, which should be construed in an illustrative and not limiting sense as follows:

DETAILED DESCRIPTION OF THE PREFERRED EMBODIMENTS

In accordance with the invention, methods of inhibiting bacterial exoenzymes are provided using deodorant compositions comprised of deodorant active materials, which are inhibitors of the odor-producing axillary bacterial exoenzymes, suspended or dissolved in a cosmetic vehicle.

In general the method comprises the steps of providing a cosmetic vehicle and dissolving or suspending a deodorant active material which is an inhibitor of bacterial exoenzymes responsible for the production of steroidal axillary malodor therein to produce a deodorant composition.

Bacterial exoenzymes which hydrolyze steroid esters are responsible for producing steroidal axillary odor. These exoenzymes can be any of several bacterial exoesterases, but aryl sulfatase (AS) and beta-glucuronidase (beta-G) are the primary bacterial exoenzymes responsible for producing the steroidal axillary odor.

The human body produces sterile, odorless apocrine sweat which deposits water-soluble, odorless steroid conjugates onto the hair and skin in the axilla. Bacterial exoenzymes secreted by local bacteria cause hydrolysis of these steroid conjugates to release volatile, odorous, free steroids which produce the steroidal axillary malodor.

The deodorant active materials used in the invention are inhibitors of these bacterial exoenzymes thus inhibiting hydrolysis of the steroid conjugates and preventing release of the odorous, free steroids responsible for axillary malodor. The deodorant active materials include $Cu++$, hexametaphosphate (SPORIX), D-glucaro-▲-lactone, EDTA, NTA, O-phenanthroline, Sodium sulfate or orthophosphate. The deodorant active material constitutes between 1–100% by weight of the composition.

The deodorant active material is dissolved or suspended in a cosmetic vehicle to provide a deodorant composition to prevent axillary malodor. The cosmetic vehicle can be in the form of a soap, lotion, fluid, cream, gel stick, powder or spray. The vehicle in the form of a soap or detergent comprising inorganic acids, organic acids or water soluble metal salts of fatty acids. The vehicle in the form of a lotion contains non-volatile polar or non-polar ingredients selected from the group consisting of polyhydric alcohols and emollient oils. Preferably the lotion comprises a liquid carrier of a lower alcohol or an aqueous alcoholic media. The vehicle in the form of a fluid is comprised of a suspending or thickening agent for use as a roll-on. The stick vehicle is comprised of a monohydric or polyhydric alcohol gelled with a fatty alcohol or fatty amide or combination thereof. The cream vehicle is comprised of an aqueous emulsion of a fatty material. The deodorant agent can further be suspended in a liquid vehicle comprised of a carrier liquid and a liquified gaseous propellant, in the form of a deodorant spray.

In an alternative embodiment of the invention, a cosmetic vehicle comprising inorganic acids, organic acids or water soluble metal salts of fatty acids is combined with a deodorant active material, selected from the group consisting of $Zn++$ compounds, which is an inhibitor of bacterial exoenzymes responsible for the production of steroidal axillary malodor. The deodorant active material is dissolved or suspended in the cosmetic vehicle to produce a deodorant composition which prevents steroidal axillary malodor. Any Zn++ compound may be employed in the invention if it is stable at the pH of the final composition and if it provides adequate levels of free Zn++ ions. A preferred deodorant active material is zinc-glycinate. Preferably, the deodorant active material constitutes over 50% by weight of the deodorant composition. The cosmetic vehicle of this embodiment can also be in the form of a soap, lotion, fluid, cream, gel stick, powder or spray.

In the following examples methods for inhibiting bacterial exoenzymes responsible for the production of steroidal axillary malodor are shown. Example I shows various inhibiting compounds which inhibit bacterial exoenzymes from hydrolyzing steroid esters thus preventing the production of steroidal axillary odor. Example II shows production of deodorant compositions according to the invention comprising deodorant active materials, which are inhibitors of odor producing axillary bacterial exoenzymes, suspended or dissolved in a cosmetic vehicle. These examples are merely representative and are not inclusive of all the possible embodiments of the invention.

EXAMPLE I

Various inhibiting compounds of bacterial exoenzymes, aryl sulfatase (AS) and beta-glucuronidase (beta-G), responsible for the production of axillary malodor were tested. Several inhibiting compounds were found which functioned in the axilla to prevent the generation of odor rather than to mask it, inhibit perspiration, or disturb the indigenous microflora. These deodorant active materials which inhibit the bacterial exoenzymes can be incorporated as an active agent into cleansing formulations to prevent the production of axillary odor.

MATERIALS

B-glucuronidase from *E. coli* and aryl sulfatase from *Aerobacter aerogenes*, 4-methyl umbelliferyl glucuronide, 4-methylumbelliferyl sulfate, 4-methylumbelliferone, and D-saccharic acid-▲-lactone were purchased from Sigma Chemical Co. Sodium hexametaphosphate (SPORIX) was obtained from International Sourcing.

Apocrine secretion fluid was collected from eleven subjects. The axillary area was shaved, washed with a 0.1% solution of Triton X-100, rinsed with water, blotted dry, then rinsed with hexane. An intradermal injection of 0.1 ml of 1:2000 adrenaline was performed to stimulate the apocrine glands. Micropipettes (10 µl) were placed directly against the skin to collect the droplets of apocrine secretion. Samples were frozen until ready for use. The samples were eluted from the capillary tubes with 0.1M Tris buffer, pH 7.0, when ready for use in the odor-generation studies. Lipophilic diphtheroid cultures isolated from human axillae were obtained.

Zinc glycinate was prepared by combining: 52.5 g (0.6 mol) glycine and 20.35 g (0.25 mol) ZnO and stirring in 300 g water at 75° C. until a clear solution was obtained. After cooling the product was precipitated with 300 g of ethanol. The white crystals were washed three times with absolute ethanol and dried in vacuo. Zinc as determined by atomic absorption was 27% (theoretical 30%) and glycine by Kjeldahl was 68% (theoretical 70%). Solubility of zinc glycinate (Zn-GLY) in water at 20° C. and pH 7.2 was found from zinc concentration of a saturated solution to be 5 g/100 ml.

PILOT STUDY

A double-blind screening study was designed to determine whether bacteria in the axilla provided the exoenzymes beta-G and AS in axillary secretions. These enzymes can be detected with synthetic substrates 4-methylumbelliferyl glucuronide (4-MUG) and 4-methylumbelliferyl sulfate (4-MUS), respectively, both of which release fluorescent 4-methylumbelliferone (4-MU) upon hydrolysis, as shown below. These fluorogenic substrates are models of the steroid glucuronides and sulfates.

Swabs were taken from the axillae of twenty men, classified by professional odor evaluators [Hilltop Laboratories, Cincinnati, Ohio] as 10 "high-odor formers" and 10 "low-odor formers." Trypticase soy agar plates were prepared containing either 4-MUS (substrate for aryl sulfatase) or 4-MUG (substrate for beta-glucuronidase) at a concentration of 25 ppm. Elutions of the swabs were plated on both substrates, incubated for 24 hours and the fluorescence of the plates was estimated visually.

The double-blind screening was designed to detect the presence of exoenzymes in axillary secretions. On plates designed to test for beta-G, ten sweat samples gave high fluorescence; nine of these came from "high-odor formers." Only one came from a "low-odor former." On plates designed to test for AS, six of eight "high-odor formers" were found to have swabbings containing AS (two samples were lost), and only two of the ten "low-odor formers" had the enzyme. These results show that some axillary bacteria generate steroid esterases and that the presence of these enzymes may be correlated with axillary odor.

SEMIQUANTITATIVE ASSAYS OF BETA-GLUCURONIDASE AND ARYL SULFATASE

Semiquantitative assays of the exoenzymes beta-G and AS were prepared. The enzyme assays measure conversion at 37° C. of the non-fluorescent substrates 4-MUG (for beta-G) and 4-MUS (for AS) to fluorescent product, 4-MU. The assay mixtures contained:

| FOR BETA-G | FOR AS |
| --- | --- |
| 0.65 ml water | 1 ml water |
| 0.5 ml 0.1M Tris buffer, pH 7 | 1.7 ml 0.1M Tris buffer, pH 7 |
| 0.25 ml 0.01 mg/ml 4-MUG in water | 0.2 ml 0.5 mg/ml 4-MUS in water |
| 0.1 ml 0.0001 mg/ml beta-G in Tris | 0.1 ml 0.01 mg/ml AS in Tris |
| 0 mg/ml beta-G/Tris as control | 0 mg/ml AS/Tris as control |

For the semiquantitative studies, fluorescence was detected by long-wave UV lamp (Black-Light Eastern Corporation Model XX 15).

The effects of inhibitors on the enzymatic reactions were assessed by substituting aqueous solutions of test inhibitor, at 0.1 mM to 100 mM, for the water. To rule out quenching of the fluorescence reaction by the inhibitors separate tests were performed comparing the fluorescence from 4-MU at the maximum concentration expected in the enzyme reaction mixtures with either inhibitor solution or water.

Various inhibiting compounds of mammalian beta-G's and AS's, as well as related materials, were tested in the assay. The classic inhibitor of beta-G is saccharic acid-▲-lactone (glucarolactone). This material was tested as well as the simple sugars, mannose, fucose and galactosamine and the polysaccharide pullulan. One of the reported inhibitors of beta-G, EDTA, is a strong chelating agent. Also tested against the enzyme were o-phenanthroline, citrate, gluconate, nitrilotriacetate and hexametaphosophate. Table I below summarizes the results obtained with the materials tested.

TABLE I

| COMPOUNDS TESTED FOR INHIBITION OF BETA-G AND AS | | |
| --- | --- | --- |
| COMPOUND | BETA-G | AS |
| Cu++ | + | + |
| Zn++ | + | + |
| hexametaphosphate | + | + |

TABLE I-continued

| COMPOUNDS TESTED FOR INHIBITION OF BETA-G AND AS | | |
| --- | --- | --- |
| COMPOUND | BETA-G | AS |
| D-glucaro-▲-lactone | + | |
| EDTA | + | − |
| NTA | + | − |
| O-phenanthroline | + | |
| Citrate | − | |
| Sodium sulfate | + | |
| Gluconate | − | |
| Mannose | − | |
| Fucose | − | |
| Galactosamine | − | |
| Pullulan | − | |
| Orthophosphate | | + |

+ indicates enzyme inhibition
− indicates no enzyme inhibition

Several materials were found to inhibit each enzyme, but three of the agents tested—Zn++, Cu++ and hexametaphosphate—inhibited both exoenzymes beta-G and AS.

QUANTITATIVE ASSAYS OF BETA-G AND AS

In addition to the semiquantitative assays several inhibitors of each, beta-G and AS, were assayed by quantitative fluorimetry. Studies were carried out with a Perkin-Elmer model MPF-3 with an Osram XBO high pressure Xenon lamp, using quartz cuvettes only. Prior to the performance of quantitative assays it was necessary to determine absorption and emission maxima of the fluorescent product 4-MU, as well as a concentration range for which the fluorescence intensity of this species varies linearly with concentration. A solution of 4-MU, 2 μg·ml, was prepared in 0.1 M Tris buffer, pH 7.0. The absorption spectrum was scanned, giving a maximum at 334 nm. The emission maximum, 444 nm, was obtained by scanning the emission spectrum while irradiating at 334 nm. All quantitative fluorescence studies employed these parameters.

Figure 1:
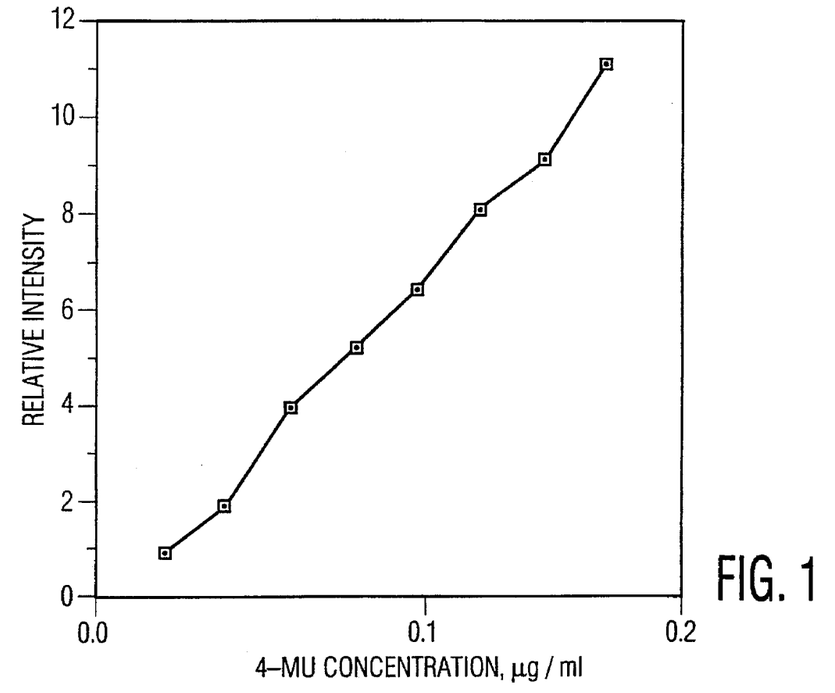
FIG. 1 is a graphic illustration of fluorescence as a function of 4-methylumbelliferol (4-MU) concentration.

Linear calibration curves as shown in FIG. 1 were generated for the concentration ranges, (1) 0.2 μg/ml–2.0 μg/ml and (2) 0.02 μg/ml–0.2 μg/ml. The levels of 4-MU generated in beta-G and AS assays fell into range 1. The conversion factor was 1 fluorescence unit=0.09 μM 4-MU.

Samples were prepared as described above. All components, except the enzyme, were warmed to 37° C. before addition of the enzyme. During the assays, reaction mixtures were maintained at 37° C. Fluorescence intensities were measured as a function of time.

Figure 2:
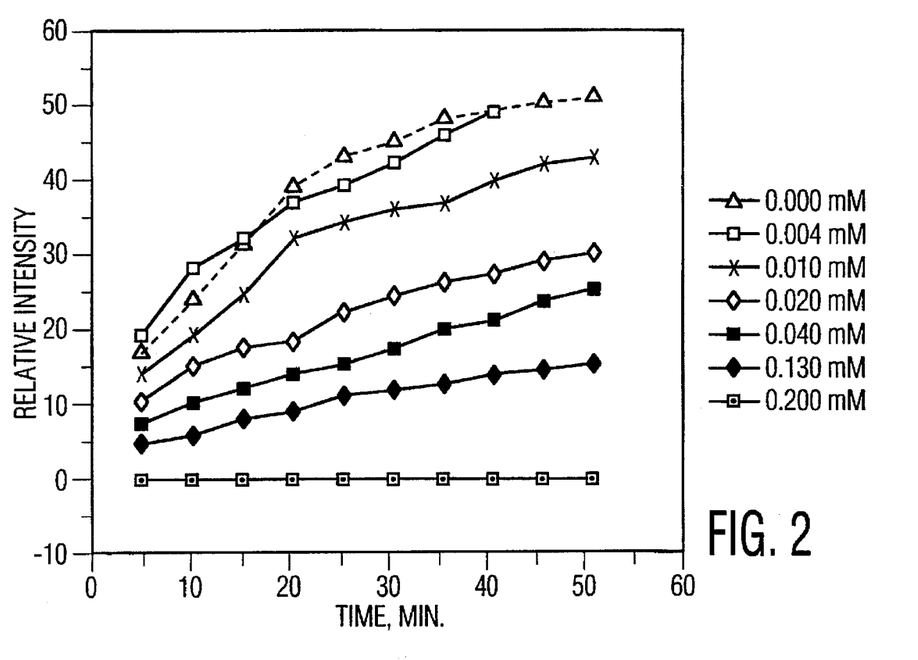
FIG. 2 is a graphic illustration of the inhibition of beta-glucuronidase by glucarolactone.

The effects of five inhibitors of beta-G, i.e. Cu++, Zn++, D-glucaro-▲-lactone, EDTA and o-phenanthrolone, and three inhibitors of AS, i.e. Cu++, Zn++ and hexametaphosphate, identified in the semi-quantitative assays, as shown in Table I, were studied quantitatively in fluorescence assay. As in the semi-quantitative tests, the progress of the reactions was indicated by the development of fluorescent product 4-MU from the non-fluorescent substrates, 4-MUG and 4-MUS. The data was recorded as fluorescence emission intensity as a function of time. A representative example of the results of these assays is given in FIG. 2 which shows the effect of glucarolactone concentration upon beta-G activity. Similar plots were constructed for each inhibitor. At each concentration, the beginning slope indicates the initial reaction rate. These rates were then expressed as a fraction of the uninhibited reaction rate and plotted against the log of the inhibitor concentration. See FIGS. 3 and 4.

Figure 3:
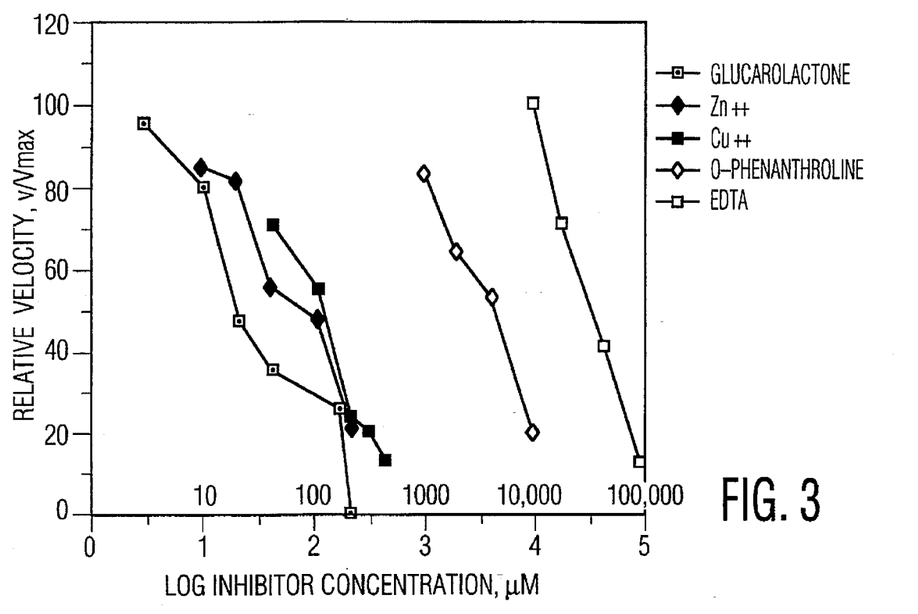
FIG. 3 is a graphic illustration of the inhibition of beta-glucuronidase, showing a decrease in relative reaction velocity with increasing concentration of five inhibitors.

In FIG. 3, for beta-G, the glucarolactone was the most effective inhibitor, (1–10 µm range). The divalent cations, Zn++ and Cu++ were effective at approximately 10–100 µM. The sequestering agents EDTA and phenanthroline were significantly less effective, providing inhibition at millimolar levels.

Figure 4:
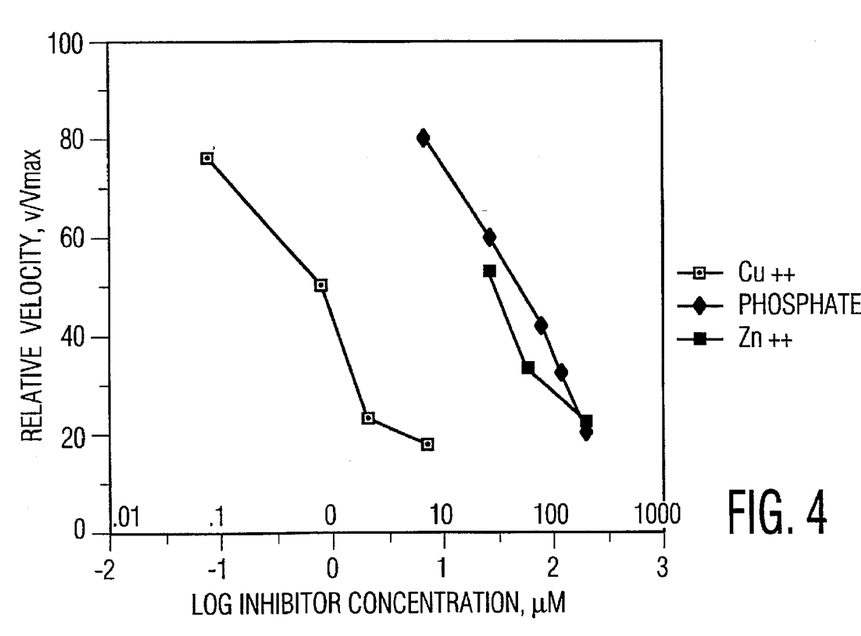
FIG. 4 is a graphic illustration of aryl sulfatase, showing a decrease in relative reaction velocity with increasing concentration of three inhibitors.

For the exoenzyme AS, the Cu++ ion was the most effective inhibitor, (0.1–10 µM range). Zn++ and phosphate were effective at 10–100 µM.

Most microbial AS belong to the Type I class, which is not inhibited significantly by sulfate or phosphate, but the AS of *Aerobacter aerogenes* is somewhat more sensitive than that of other bacteria. This property is apparent since phosphate was found to be about as effective as the zinc cation.

These results indicate that at least some bacterial beta-G and AS can be inhibited by Zn++, Cu++, chelating agents or glucarolactone.

ODOR PRODUCTION IN APOCRINE SECRETION

Inhibiting compounds were then tested to determine their effect on odor production in apocrine secretion. Sterile, odorless apocrine secretion was eluted from capillaries into 1.5 ml of 0.1M Tris buffer, pH 7.0. In the first study, apocrine sweat was treated with beta-glucuronidase, (*E. coli*) and aryl sulfatase (*Aerobacter aerogenes*) at 0.01 mg/ml in Tris buffer, 0.1M, pH 7.0. The apocrine secretion was also treated with the lipophilic diphtheroid and with a mixed culture of axillary bacteria, each in sterile saline suspension.

In a second study, inhibitors of the two enzymes were included in the reaction mixtures—Zn++ as Zn-Glycinate, saccharic acid lactone and hexametaphosphate. The concentration of each inhibitor used in this study was 40 mM.

Samples were prepared in gas chromatography vials and sealed with crimp caps. Samples were incubated at 37° C. In the first study, odor evaluations were conducted at 16 hr and 40 hr of incubation. In the second study, odor evaluations were conducted at 24 hr and 48 hr of incubation. Odor evaluations were performed by a panel of five individuals, including one professional perfumer.

In the preliminary tests, mixed cultures of axillary bacteria converted 4-MUG to 4-MU, as judged from the appearance of visible fluorescence. This result demonstrated that one or more strains of axillary bacteria were generating beta-G. This experiment tested the theory that the activity of this enzyme upon certain steroid conjugates present in sweat might produce axillary odor. Sterile, odorless, apocrine secretion was then treated with the individual bacterial enzymes, beta-glucuronidase and aryl sulfatase and also with lipophilic diphtheroid and a mixed culture of axillary bacteria in sterile saline suspension. The results of the first study are given below in Table II.

TABLE II

| ODOR GENERATION IN APOCRINE SWEAT | |
|---|---|
| MATERIAL | ODOR |
| APOCRINE SWEAT* | Faint, musky |
| BETA-G | No odor |
| APOCRINE SWEAT + BETA-G | Strong, musky and sweaty |
| AS | No odor |
| APOCRINE SWEAT + AS | Moderate, musky and sweaty |
| LIPOPHILIC DIPHTHEROID* | Faint moderate off-odor |
| APOCRINE SWEAT + LIPOPHILIC DIPHTHEROID | Strong, musky and sweaty |
| MIXED BACTERIA* | Moderate malodor |
| APOCRINE SWEAT + MIXED BACTERIA | Strong malodor, sweaty note |

*Controls

Neither apocrine sweat nor either of the pure enzymes exhibited odor. Cultures of lipophilic diphtheroid, and a mixed axillary population had the faint-to-moderate malodor characteristic of any bacterial culture, but no particular "sweaty" odor. However, when apocrine sweat was mixed with either enzyme or with either bacterial culture, a strong sweaty odor was produced.

ENZYME ACTIVITY IN CELL-FREE MEDIA

As a control the following test was performed to determine exoenzyme activity in a cell-free culture medium. Lipophilic diphtheroid was grown for 18 hr in brain-heart infusion containing 0.1% Tween 80, centrifuged for 20 min., and the supernatant medium was filtered through a 0.22 micron filter which retains bacteria. The substrate solution (2 ml of 4-MUG or 4-MUS) was mixed with 1 ml of the sterile filtered medium (or water as control).

To confirm and characterize the implication of lipophilic diphtheroids, the enzyme substrates were exposed to cell-free culture medium. The medium exhibited both aryl sulfatase and beta-glucuronidase activity.

The fact that the odor can be produced by the enzymes alone indicates that it is their very activity that is the essential cause of steroidal axillary malodor. The fact that the odor is produced by lipophilic diphtheroids alone suggests that this strain may be one member of the population that produces the enzymes and accounts for its implication in odor production. The presence of enzyme activity in cell-free diphtheroid medium shows that the enzymes are extracellular.

The sterile secretion alone generated a faint musky odor after incubation at 37° C. Further tests were performed to determine indigenous beta-G and AS activity. Addition of 4-MUG, the beta-G substrate, produced the characteristic 4-MU fluorescence, but addition of 4-MUS, the AS substrate, had no effect.

INHIBITION OF ODOR FROM APOCRINE SECRETION

Results of the second study are presented in Table III below. The odor was generated only in those samples containing either apocrine secretion together with AS and beta-G enzymes or apocrine secretion with bacteria. Zinc glycinate was highly effective in preventing odor; the odor-inhibiting effect of the lactone, although significant, was weaker than that of zinc glycinate in both systems; the polyphosphate (SPORIX) had no effect. This is probably due to the fact that polyphosphates are hydrolyzed in aqueous solution and possibly SPORIX was degraded to inactive fragments during incubation. The polyphosphates showed the weakest beta-G inhibition in Table I.

TABLE III

IN VITRO DEODORANT ACTION OF ENZYME INHIBITORS

| MATERIALS | ODOR |
|---|---|
| ENZYMES* | No odor |
| APOCRINE SWEAT | No odor to faint off-odor |
| ENZYMES* + APOCRINE SWEAT | Faint/moderate musky-sweaty |
| ENZYMES* + SWEAT + ZnGLY | No odor |
| ENZYMES* + SWEAT + SPORIX | Faint/moderate musky-sweaty |
| ENZYMES* + SWEAT + LACTONE | No odor to faint musky-sweaty |
| LIPOPHILIC DIPHTHEROIDS (LD) | Faint off-odor |
| LDs + APOCRINE SWEAT | Strong, sweaty |
| LDs + SWEAT + ZnGLY | Faint stale musky |
| LDs + SWEAT + LACTONE | Moderate sweaty |

*Enzymes are a mixture of AS and beta-G

It has been recognized that axillary odor arises from the interaction of bacteria with apocrine sweat. A class of volatile free steroids has been associated with axillary odor and with a particular bacterial population—the lipophilic diphtheroids. The enzymes responsible for this process are capable of releasing free volatile steroids from odorless steroid conjugates present in sterile apocrine secretion.

From the test of this Example it is shown that a mixed culture of axillary bacteria produced a beta-glucuronidase capable of cleaving asteroid glucuronide. From the screening tests it was shown that another class of hydrolytic enzyme, aryl sulfatase, was also present in the axillary strains.

It was further shown that a beta-glucuronidase and an aryl sulfatase, both of bacterial origin, will cleave odorless compounds in sterile secretion to produce distinct axillary odor, thus implicating the hydrolytic enzymes in the release of odor. In addition, a lipophilic diphtheroid secretes both of the enzymes necessary to produce steroid malodor from sterile axillary secretion.

The generation of odor from the addition of beta-glucuronidase or aryl sulfatase or lipophilic diphtheroid to apocrine secretion, can be prevented by the inclusion of the enzyme inhibitor Zn++ and somewhat reduced by glucarolactone, which inhibits only the beta-G but not the AS. This further substantiates the role of these bacterial enzymes in axillary odor.

Thus, deodorant active materials, comprised of Cu++, Zn++, hexametaphosphate, glucarolactone, EDTA, NTA, o-phenanthroline, sodium sulfate of orthophosphate, which are inhibitors of these bacterial exoenzymes responsible for the production of steroidal axillary malodor can be incorporated into deodorant compositions to prevent the production of axillary odor.

EXAMPLE II

The following experiments show production of deodorant compositions according to the invention comprising deodorant active materials which are inhibitors of odor producing axillary bacterial exoenzymes. The deodorant active materials tested include zinc ions as contained in aqueous zinc-glycinate solutions.

In general, zinc from aqueous zinc glycinate binds to hair and skin at pH 7. The binding increases with Zn concentration becoming appreciable when Zn exceeds about 1 millimole/liter. In the presence of soap or synthetic detergents, Zn binding still occurs, but at a lower level.

Zinc bound to hair acts as an effective inhibitor of two bacterial exoenzymes, aryl sulfatase and beta-glucuronidase, which are implicated in the production of steroidal axillary malodor. Clinical testing of the deodorant activity of this material has shown that a 4.5% solution of Zn-GLY is as effective as 5% aluminum chlorohydrate in controlling axillary odor. Although zinc glycinate is slightly bactericidal, enzyme inhibition seems to be the principal mechanism of deodorancy.

MATERIALS

Enzymes, substrates and buffer components were purchased from Sigma Chemical Co. All experiments were carried out in 0.1M Tris buffer at pH 7.

Non-isotopic Zn-GLY and $\{^{65}Zn\}$ Zn-GLY was prepared as needed for each experiment. A convenient amount of $^{65}Zn$, in solution of negligible volume and containing negligible mass of $^{65}Zn$, was added to a solution of non-isotopic $ZnCl_2$ at a concentration twice what was necessary for the experiment. An equal volume of solution containing a two-fold molar excess of glycine sodium salt was added to it, so that the final Zn concentration was as required. The mixture had a pH of 9. The precipitate (ZnO), which formed when glycine was first added, gradually redissolved as the complex formed and the final solution contained the required concentration of Zn in solution as the diglycinate at a pH of approximately 8.

INSTRUMENTATION

Radioisotope was detected by counting in a Baird Atomic Model 530 Gamma Spectrometer with multichannel analyzer. Fluorescence intensities were measured with a Perkin-Elmer Model MPF-3 with an Osram XBO high-pressure Xenon lamp, using quartz cuvettes. Absorption wavelength for 4 methylumbelliferol was 334 mm; emission wavelength was 444 mm.

KINETICS OF BINDING OF Zn-GLY TO HAIR

Before undertaking quantitative substantivity studies, it was necessary to establish the time scale of binding Zn to the substrate. Solutions of $\{^{65}Zn\}$ Zn-GLY were prepared as above, with Zn at 0.01 mM, and 10 mM; hair samples (0.1 g each) were exposed to 2.5 ml of solution for various lengths of time. The solution was decanted, the hair rinsed twice with 0.5 ml water, and the rinses combined with the exposure solutions. Radioactivity in the solution ("unbound isotope") and in hair ("bound isotope") was counted. The amount of Zn μmol bound/g hair and the percent of radioactivity ultimately bound to hair was calculated from the total Zn in the sample solutions.

Figure 5:
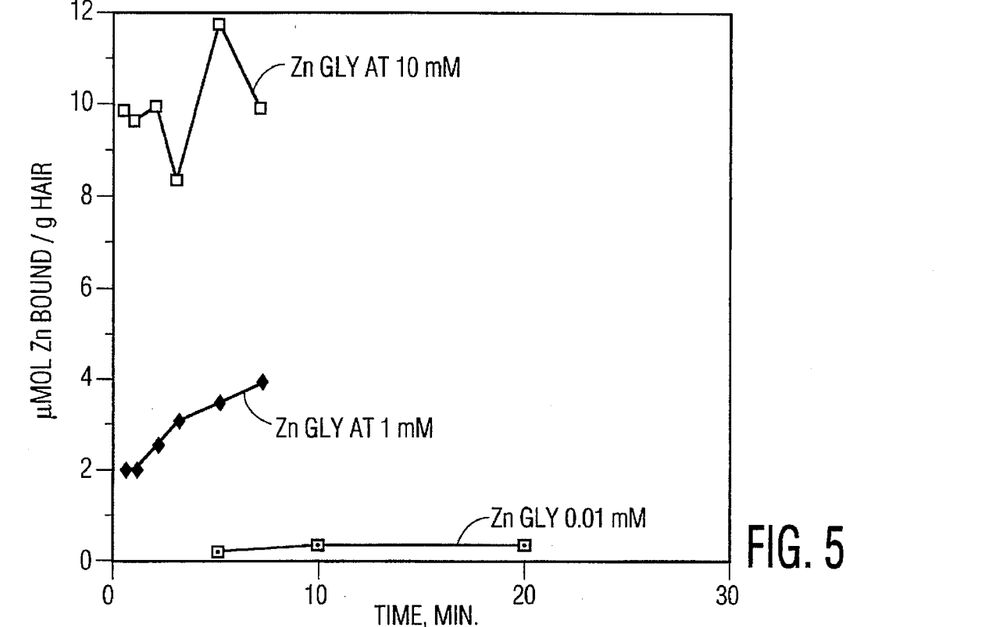
FIG. 5 is a graphic illustration of the kinetics of binding Zn-GLY to hair.

FIG. 5 shows that for Zn concentration exceeding 1 mM, binding is near equilibrium after an hour and that hair can hold at least 10 μmol of Zn. Subsequent experiments were conducted using overnight incubation of Zn-GLY with substrate.

To maintain lasting deodorancy, an active deodorant agent must bind to the skin and/or hair and the bound residue must remain inhibitory in the presence of soaps or other materials. The following tests were performed to determine the substantivity of zinc ions to hair and skin.

SUBSTANTIVITY OF Zn-GLY TO HAIR: EFFECTS OF GLYCINE

The effects of the presence of glycine on the substantivity of zinc glycine to hair was tested. Two series of solutions were prepared with various levels of Zn in both; one series had excess glycine present, the other had none. See FIG. 6. Two ml of each solution was allowed to equilibrate with 0.1 g hair for two hours and the quantity of Zn in µmoles bound/g hair was calculated.

Figure 6:
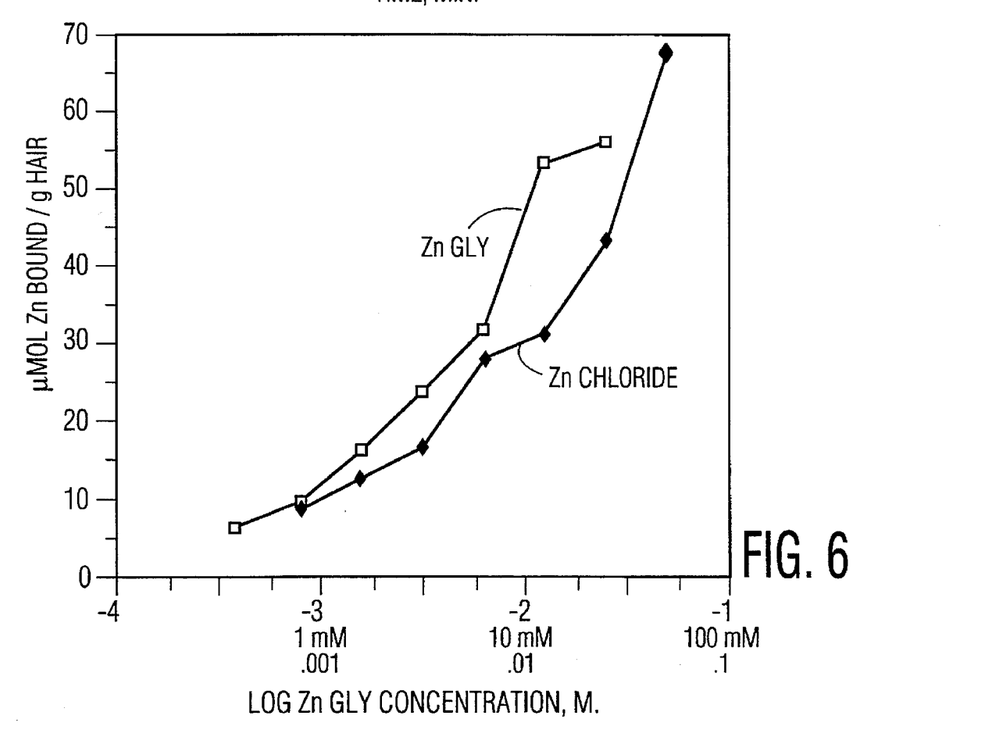
FIG. 6 is a graphic illustration of the binding of zinc glycinate to hair, in concentration dependence.

The effect of complexation of the Zn ion on its substantivity to hair was investigated by measuring the binding of Zn from zinc chloride in the presence and absence of glycine. FIG. 6 shows that Zn is bound to hair more efficiently when glycine is present. Apparently, Zn-GLY binds to keratin with somewhat higher affinity than Zn chloride.

This study indicates that the formation of Zn-GLY is proceeding in the solution and that the Zn from Zn-GLY binds appreciably to hair from solutions where Zn-GLY concentration exceeds approximately 1 mM. FIG. 6 particularly shows that for Zn-GLY at a concentration of 1 mM binding of Zn to hair is approximately 10 µmol/g. When Zn-GLY expressed as {Zn} exceeds about 10 mM in solution, binding is about 50 µmol/g.

SUBSTANTIVITY OF Zn-GLY TO SKIN

The substantivity of zinc glycine to skin was tested. Two pieces of stratum corneum, 50 mg each, were exposed to 2 ml of 50 mM {$^{65}$Zn} Zn-GLY while two pieces were exposed to 2 ml of 0.01 mM {$^{65}$Zn} Zn-GLY. After decanting, the stratum corneum pieces were rinsed twice with water, and the rinsings were saved and counted with the solutions and stratum corneum samples.

Table IV below shows that stratum corneum exposed to 50 mM Zn-GLY binds approximately 90 µmol Zn/g. Exposure to 0.01 mM Zn-GLY produces binding of less than 1 µmol/g. Interestingly, the binding to the stratum corneum is about the same as the binding to hair. Apparently, the keratins of both are similar with respect to chemical features recognized during zinc glycinate binding.

TABLE IV

DEPOSITION OF Zn—GLY ONTO STRATUM CORNEUM
(µmol Zn—GLY/g stratum corneum)

| {Zn—GLY} | Trial 1 | Trial 2 | Average |
|---|---|---|---|
| 0.01 mM | 0.3 | 0.3 | 0.3 |
| 50.0 mM | 82.0 | 108.0 | 95.0 |

INHIBITORY ACTIVITY OF RESIDUES

The inhibitory effect of zinc glycinate on the activity of the enzymes AS and beta-G was measured quantitatively using the fluorogenic substrates 4-MUS and 4-MUG, respectively. A set of 100-mg samples of hair that had been exposed to various levels of Zn-GLY was washed to remove unbound Zn-GLY and then was split in half. One half was placed in reaction mixtures with AS (0.001 mg)/4-MUS (0.1 mg) in 2 ml Tris buffer. The other half was placed in reaction mixtures with beta-G (0.0001 mg)/4-MUG (0.0025 mg) in 2 ml Tris buffer. Reaction mixtures were incubated and irradiated at 334 nm. Fluorescence emission intensity at 444 nm was monitored over a period of one hour as described previously.

These tests show that exposure to a solution of 100 mM Zn-GLY is required to produce a residue of approximately 100 µmol/g of Zn per gram of hair or skin. The following experiments were performed to determine whether the residue left by such solutions was an effective inhibitor of the enzymes responsible for axillary odor generation.

Figure 7:
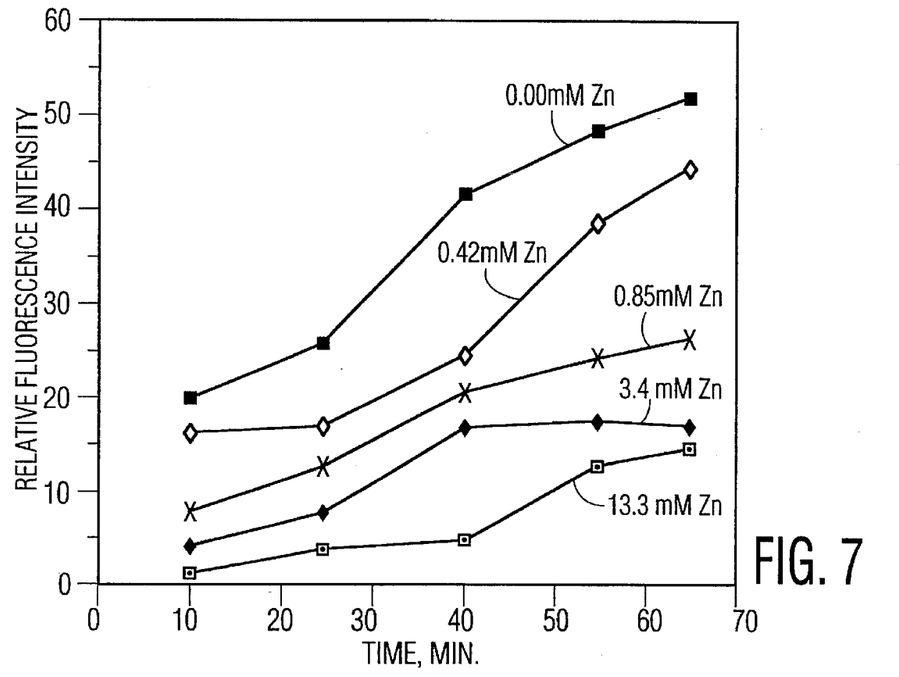
FIG. 7 is a graphic illustration of Beta-G reaction in the presence of hair treated with Zn-GLY.
Figure 8:
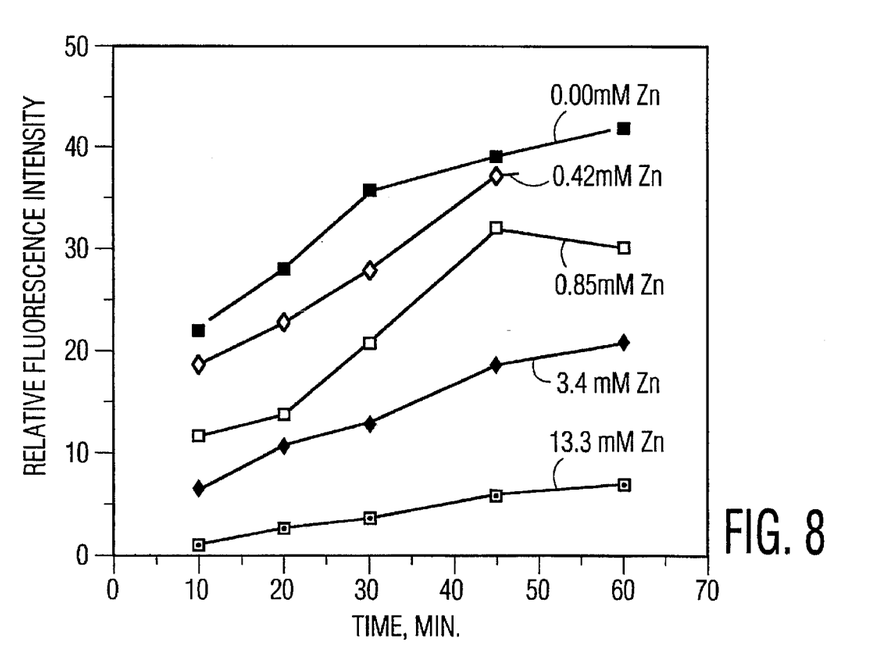
FIG. 8 is a graphic illustration of aryl sulfatase reactions in the presence of hair treated with Zn-GLY.
Figure 9:
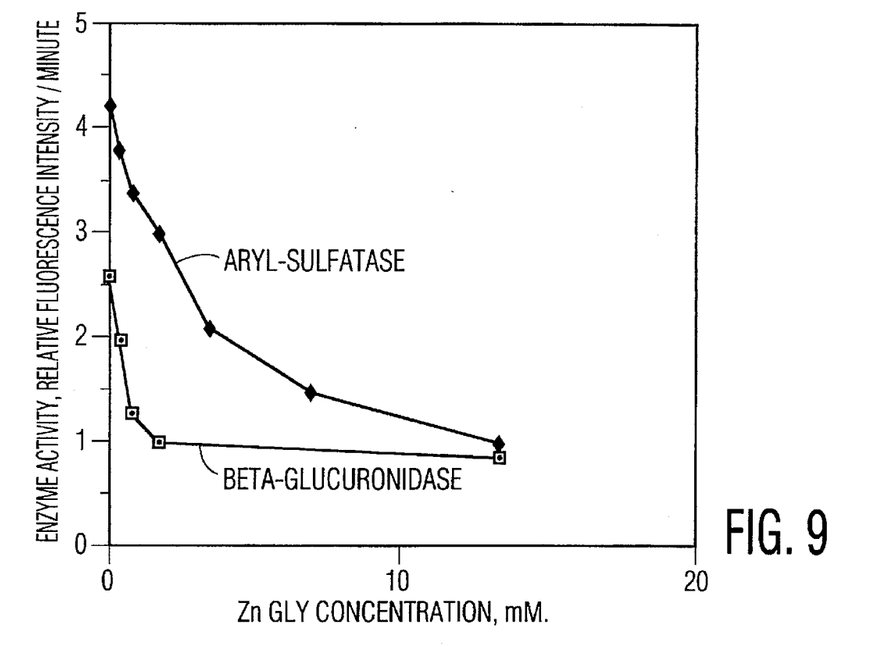
FIG. 9 is a graphic illustration of the inhibition of odor-causing enzymes by hair exposed to various levels of Zn-GLY.

FIG. 7 shows the time courses for beta-G reactions in the presence of the hair samples that had been exposed to various concentrations of Zn-GLY. FIG. 8 is a similar plot for AS reactions. In both, it is obvious that the inhibition of the reactions is dependent on the concentration of bound Zn. Replotted as enzyme activity vs {Zn} (see FIG. 9), the data show that hair exposed to Zn-GLY at less than 15 mM inhibits AS by more than 90%, and that hair exposed to less than 10 mM Zn-GLY inhibits beta-G almost completely.

COMPATIBILITY WITH SOAP PRODUCTS

In testing the effectiveness of the inhibiting characteristics of the deodorant active materials in the presence of soaps, solutions of {$^{65}$Zn} Zn-GLY were prepared at 0.1M and 0.5M Zn in water, and also in solutions of soap and of syndet bar at various concentrations. Samples of chopped hair (0.1 g each) were then exposed to 2 ml of each of these solutions for various time periods, ranging from minutes to hours.

Once Zn++ is bound to the skin or hair the presence of soap or detergent solutions will not remove the bound Zn++. Zn++ from high concentrations of Zn-GLY (0.5M) precipitates from soap solution, probably as Zn fatty acid salt. Such insolubility suggests that Zn residues on the skin (from a deodorant preparation) would not be removed by soap or syndet washing, and might provide enduring inhibition of the odor-causing enzymes.

Figure 10:
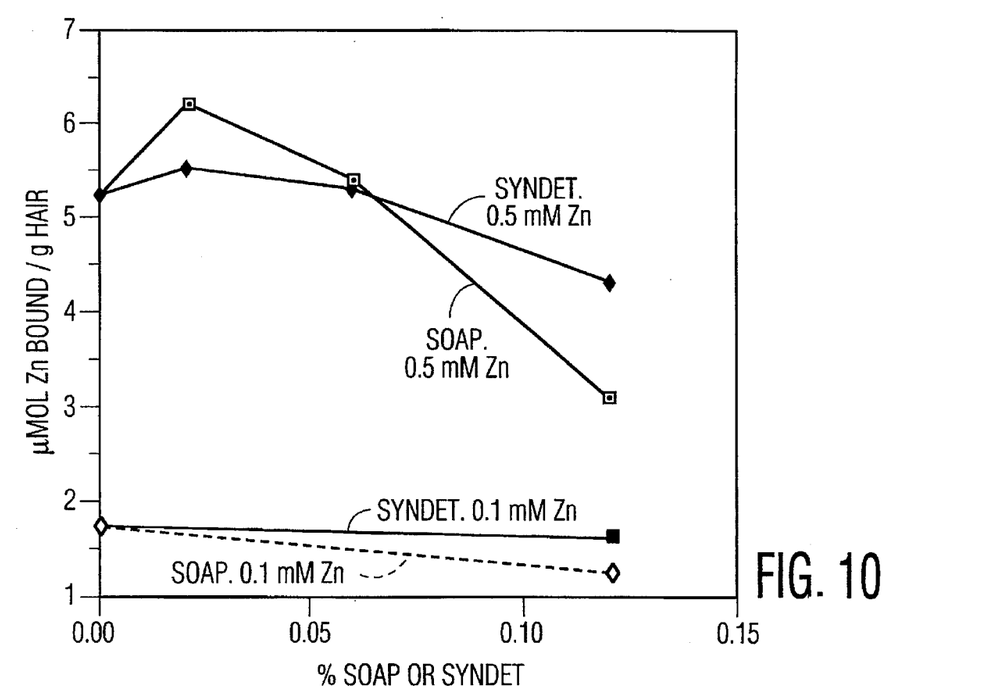
FIG. 10 is a graphic illustration of the reduced binding of Zn-GLY to hair from soap and syndet compositions.

In addition, the presence of soap or detergent solutions does not interfere with the binding of Zn++ onto the skin or hair. Low concentrations of $^{65}$Zn-labeled Zn-GLY were suspended in soap and syndet solutions, exposing fresh hair samples to the solutions, and measuring the $^{65}$Zn residue on the hair. FIG. 10 shows that dissolved synthetic detergent bar reduces the binding of Zn-GLY and that soap reduces it even more. However, neither soap nor syndet eliminates binding. More than half the Zn bound from water at any Zn concentration tested is bound from test solutions of soap and syndet.

CLINICAL STUDIES: AXILLARY DEODORANCY OF Zn-GLY

A complete human clinical study was conducted [by Hill Top Biolabs, Inc., of Cincinnati, Ohio] to assess the deodorant efficacy of zinc glycinate. The test solution was 4.5% Zn-GLY (1.5% Zn); this level represents the maximum solubility of Zn-GLY in aqueous solution. The positive control was 5% aluminum chlorhydrate, a level that effects deodorancy by antimicrobial action but does not inhibit perspiration. The negative control was water. Odor assessments were performed by four experienced professional evaluators from Hill Top Research, using a ten-point scoring system. Ninety subjects were recruited, and baseline scores were established after a twenty-four hour conditioning period. Sixty subjects with highest scores (all greater than 4) were retained for the study. Thirty subjects were assigned to Group I, to test Zn-GLY in one axilla, versus water in the other; thirty were assigned to Group II, testing aluminum chlorhydrate in the same way. Half of each group had the right axilla treated with the compound and the other half had the left axilla treated.

During the test the subjects were entered into a regimen of timed, supervised washes with conditioning soap bars, followed by supervised treatments with the test solutions and post-treatment odor evaluation. The evaluations were conducted at 5-hr and 24-hr intervals following treatments 2, 3 and 4 and all aspects were randomized to eliminate any biases.

Scores of the four judges were averaged for each person, for each evaluation. The axilla-to-axilla difference for each person was taken as the index of the deodorancy of the test material versus the water control.

Based on the in vitro studies involving compatibility with soap products, which suggested that Zn-GLY could be an effective deodorant, these clinical studies assessed the deodorant efficacy of Zn-GLY. A test solution of 1.5% in Zn (4.5% Zn-GLY) was employed; this level represents the maximum solubility of Zn-GLY in aqueous solution. The positive control was 5.0% aluminum chlorhydrate. At this level the aluminum compound effects deodorancy via antimicrobial action but does not inhibit perspiration. The negative control was distilled deionized water.

A summary of the results of the deodorancy study is given in Table V below. The mean odor scores represent the four-judge average odor scores, post-treatment. The control values are the average baseline odor scores for the various cells.

TABLE V

SUMMARY OF RESULT OF DEODORANCY STUDY

|  | 5 hr | | 24 | |
|---|---|---|---|---|
| APPLICATION #2 | Zn—GLY | $H_2O$ | Zn—GLY | $H_2O$ |
| Mean Odor Score | 3.12 | 4.03 | 3.34 | 4.65 |
| % Difference | | 22.6% | | 28.1% |
|  | ACH | $H_2O$ | ACH | $H_2O$ |
| Mean Odor Score | 3.13 | 4.75 | 3.91 | 5.41 |
| % Difference | | 34.0% | | 27.8% |
| APPLICATION #3 | Zn—GLY | $H_2O$ | Zn—GLY | $H_2O$ |
| Mean Odor Score | 2.33 | 3.47 | 3.27 | 4.70 |
| % Difference | | 32.7% | | 30.5% |
|  | ACH | $H_2O$ | ACH | $H_2O$ |
| Mean Odor Score | 2.95 | 4.15 | 3.88 | 5.24 |
| % Difference | | 28.8% | | 26.1% |
| APPLICATION #4 | Zn—GLY | $H_2O$ | Zn—GLY | $H_2O$ |
| Mean Odor Score | 2.60 | 3.94 | 3.11 | 4.74 |
| % Difference | | 34.0% | | 34.5% |
|  | ACH | $H_2O$ | ACH | $H_2O$ |
| Mean Odor Score | 2.90 | 4.45 | 3.64 | 5.16 |
| % Difference | | 34.9% | | 29.5% |

% Difference represents the decrease in odor
Baseline odor scores Zn—GLY, 6.41; $H_2O$, 6.42 ACH, 6.64; $H_2O$, 6.73
Zn—GLY concentration: 4.5%
ACH (aluminum chlorhydrate) concentration: 5.0%

Zinc glycinate (4.5%) was significantly more effective than $H_2O$ in controlling malodor at each post-treatment evaluation. Aluminum chlorhydrate (5.0%) was significantly more effective than $H_2O$ in controlling malodor at each post-treatment evaluation.

The study does not include a comparison between the deodorant efficacies of Zn-GLY and aluminum chlorhydrate.

A statistical analysis was performed with the results given in Table VI. The group receiving Zn-GLY treatment exhibited lower mean odor scores than did the group receiving aluminum chlorhydrate treatment at all six evaluations. Of these six differences, four were significant: all three 24-hr evaluations gave significant differences. Only one of the 5-hr evaluations gave significant differences. Zn-GLY appears to provide a stronger and more long-lasting deodorant effect than does aluminum chlorhydrate at these levels.

TABLE VI

STATISTICAL ANALYSIS OF DEODORANT EFFECT OF Zn—GLY vs ALUMINUM CHLORHYDRATE

|  | Mean Odor Score | Significance level |
|---|---|---|
| APPLICATION #2 | | |
| 5 hr | | |
| Zn—GLY | 3.12 | 0.945 |
| ACH | 3.13 | |
| 24 hr | | |
| Zn—GLY | 3.34 | 0.003 |
| ACH | 3.91 | |
| APPLICATION #3 | | |
| 5 hr | | |
| Zn—GLY | 2.33 | 0.005 |
| ACH | 2.95 | |
| 24 hr | | |
| Zn—GLY | 3.27 | 0.003 |
| ACH | 3.88 | |
| APPLICATION #4 | | |
| 5 hr | | |
| Zn—GLY | 2.60 | 0.155 |
| ACH | 2.90 | |
| 24 hr | | |
| Zn—GLY | 3.11 | 0.044 |
| ACH | 3.64 | |

ANTIMICROBIAL PROPERTIES OF ZINC GLYCINATE

Minimum Inhibitory Concentration (MIC) values of several zinc complexes were measured for three organisms that occur naturally in the axilla: *S. epidermidis*, *S. aureus* and a lipophilic diphtheroid.

Simple salts of zinc are known to be bacteriostatic. An outcome of the experiments was producing a method to reduce axillary odor without destroying the natural flora of the axilla. Therefore MIC values of several zinc complexes and the antiseptic Irgasan DP 300 (positive control) were measured against several organisms that occur naturally in the underarm, including *S. epidermidis*, *S. aureus*, and a lipophilic diphtheroid. The results are shown in Table VII. The ">" signs indicate that bacterial growth occurred at the highest concentration of zinc compound. None of the zinc compounds were conspicuously inhibitory, having effective levels ranging from 0.1 to 1%. Thus zinc compounds exhibit very weak antimicrobial activity.

TABLE VII

MINIMUM INHIBITORY CONCENTRATIONS OF ZINC COMPOUNDS AGAINST VARIOUS BACTERIA (MIC ppm)

| COMPOUND | LIPOPHILIC DIPHTHEROID | STAPHYLOCOCCUS EPIDERMIS | STAPHYLOCOCCUS AUREUS |
|---|---|---|---|
| $ZnCl_2$ | >1000 | >1000 | >1000 |
| Zn—GLY | >1000 | 1000 | 1000 |
| Zn—NTA | >9600 | >9600 | >9600 |
| Zn—HEDPxz | >1000 | >1000 | >1000 |
| Zn—EDDA | >6500 | >6500 | >6500 |
| Irgasan | 16 | <0.5 | <0.5 |

Zinc, as zinc glycinate and at the levels tested in the experiments in Example II, binds rapidly to both hair and skin. Specifically, a 100 mM solution deposits approximately 100 μmol of zinc per gram of tissue. This proportion seems to be similar for both skin and hair, therefore the active property being exploited is an affinity for keratin and that skin keratin is similar to hair keratin with respect to the affinity of Zn-GLY. When hair is exposed to such levels of zinc glycinate, the zinc residue left on the hair, even after rinsing with water is sufficient to completely inhibit both of the bacterial enzymes that were previously implicated in the production of axillary odor. This result is substantiated by clinical studies that show that 4.5% zinc glycinate is superior to 5% aluminum chlorhydrate as an underarm deodorant as shown in Table VI.

Zinc glycinate functions as a deodorant active material by preventing the release of compounds that contribute significantly to axillary odor. It appears not merely to block odor receptors or mask unpleasant odor with a strong fragrance but directly inhibits their production.

A complex of zinc, in addition to allowing higher zinc concentration, may give rise to a product with long lasting deodorancy. The complex, acting as a reservoir, may release zinc as the free ion and is diluted by eccrine sweat or is consumed by the bacterial enzymes.

Although zinc glycinate has been found to inhibit bacterial growth, it is a distinctly poor bacteriostat, i.e. high concentrations are required for its effectiveness (see Table VII). Therefore the principal mechanism of axillary odor reduction with this compound is enzyme inhibition.

It will be recognized by those skilled in the art that the invention has wide application in the production of a diversity of deodorant compositions having deodorant active materials which inhibit bacterial exoenzymes responsible for the production of steroidal axillary malodor.

Numerous modifications are possible in light of the above disclosure such as application of different deodorant compositions to various vehicles to create deodorant soap, lotion, fluid, cream, gel stick, powder or spray to prevent axillary odor. In addition the deodorant active material may be incorporated into anti-perspirant products. Advantageously, the use of the deodorant compositions of the invention inhibit the bacterial exoenzymes responsible for the production of steroidal axillary malodor rather than neutralizing unpleasant odors through chemical interaction or inhibition of bacterial growth. Further advantage is obtained by the invention by not disturbing the natural flora of the axilla.

Therefore, although the invention has been described with reference to certain preferred embodiments, it will be appreciated that other composite structures and processes for their fabrication may be devised, which are nevertheless within the scope and spirit of the invention as defined in the claims appended hereto.

We claim:

1. A deodorant composition comprising:

a deodorant active material consisting of zinc glycinate having an effective amount of Zn++ ions for inhibiting bacterial exoenzymes responsible for the production of steroidal axillary malodor; and a cosmetic vehicle, comprising inorganic acids, organic acids or water soluble metal salts of fatty acids, in which said deodorant active material is dissolved or suspended therein;

wherein said Zn++ ions bind to the skin and/or hair and the bound residue remains inhibitory in the presence of soap or detergent solutions.

2. A deodorant composition according to claim 1, wherein said bacterial exoenzymes are aryl sulfatase or beta-glucuronidase.

3. A deodorant composition according to claim 1, wherein the amount of said Zn++ ions that bind to the skin or hair is at least 10 μmol/g.

4. A deodorant composition according to claim 1, wherein said deodorant active material constitutes over 50% by weight of the composition.

5. A deodorant composition according to claim 1, wherein said vehicle is in the form of a lotion comprising a liquid carrier of a lower alcohol or an aqueous alcoholic media.

6. A deodorant composition according to claim 5, wherein said lotion contains non-volatile polar or non-polar ingredients selected from the group consisting of polyhydric alcohols and emollient oils.

7. A deodorant composition according to claim 1, wherein said vehicle is in the form of a fluid comprising a suspending or thickening agent for use as a roll-on.

8. A deodorant composition according to claim 1, wherein said vehicle is in the form of a stick comprising a monohydric or polyhydric alcohol gelled with a fatty alcohol or fatty amide or combination thereof.

9. A deodorant composition according to claim 1, wherein said vehicle is in the form of a cream comprising an aqueous emulsion of a fatty material.

* * * * *